(12) United States Patent
Watson (10) Patent No.: US 12,076,044 B2
(45) Date of Patent: *Sep. 3, 2024

(54) IMAGING CANNULA WITH A HINGED TIP

(71) Applicant: INTUITIVE SURGICAL OPERATIONS, INC., Sunnyvale, CA (US)

(72) Inventor: Jason Paul Watson, San Jose, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 884 days.

This patent is subject to a terminal disclaimer.

(21) Appl. No.: 17/114,292

(22) Filed: Dec. 7, 2020

(65) Prior Publication Data
US 2021/0186558 A1    Jun. 24, 2021

Related U.S. Application Data

(63) Continuation of application No. 16/113,225, filed on Aug. 27, 2018, now Pat. No. 10,874,428.
(Continued)

(51) Int. Cl.
*A61B 17/34* (2006.01)
*A61B 1/00* (2006.01)
(Continued)

(52) U.S. Cl.
CPC ...... *A61B 17/3423* (2013.01); *A61B 1/00179* (2013.01); *A61B 1/00181* (2013.01); *A61B 1/00183* (2013.01); *A61B 1/018* (2013.01); *A61B 1/05* (2013.01); *A61B 17/3421* (2013.01); *A61B 34/35* (2016.02); *A61B 90/37* (2016.02); *A61B 17/00234* (2013.01); *A61B 2017/00473* (2013.01); *A61B 2017/00907* (2013.01); *A61B 2017/3445* (2013.01);
(Continued)

(58) Field of Classification Search
CPC ............ A61B 17/3417; A61B 17/3421; A61B 17/3423; A61B 17/3445; A61B 17/00234; A61B 2017/3433; A61B 2017/3454; A61B 90/361; A61B 90/37; A61B 1/05
See application file for complete search history.

(56) References Cited

U.S. PATENT DOCUMENTS 5,166,787 A    11/1992  Irion
5,305,121 A     4/1994  Moll
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Ellen C Hammond
(74) *Attorney, Agent, or Firm* — Haynes & Boone, LLP (57) ABSTRACT

A surgical cannula includes a camera disposed at the distal end to permit visualization of tissue. A hinge pivotably couples the camera to the cannula and permits the camera to pivot from a first position at the distal end of the cannula to a second position different than the first position at the distal end of the cannula. Some implementations include a pointed distal tip that carries the camera. Some implementations include two cameras posed back to back.

16 Claims, 7 Drawing Sheets

Related U.S. Application Data (60) Provisional application No. 62/552,014, filed on Aug. 30, 2017.

(51) Int. Cl.
    *A61B 1/018*    (2006.01)
    *A61B 1/05*    (2006.01)
    *A61B 34/35*    (2016.01)
    *A61B 90/00*    (2016.01)
    *A61B 17/00*    (2006.01)
    *A61B 34/30*    (2016.01)

(52) U.S. Cl.
    CPC ....... *A61B 2017/3454* (2013.01); *A61B 34/30* (2016.02); *A61B 2034/302* (2016.02); *A61B 90/361* (2016.02); *A61B 2090/371* (2016.02)

(56) References Cited

U.S. PATENT DOCUMENTS

| | | |
|---|---|---|
| 5,381,784 A | 1/1995 | Adair |
| 5,895,350 A | 4/1999 | Hori |
| 5,966,168 A | 10/1999 | Miyazaki |
| 6,066,090 A | 5/2000 | Yoon |
| 6,277,064 B1 | 8/2001 | Yoon |
| 6,450,950 B2 | 9/2002 | Irion |
| 8,289,381 B2 | 10/2012 | Bayer et al. |
| 8,439,830 B2 * | 5/2013 | McKinley ............ A61B 90/30 600/179 |
| 8,608,652 B2 * | 12/2013 | Voegele ................ A61B 1/303 600/210 |
| 8,944,995 B2 * | 2/2015 | Suda ..................... A61B 1/018 600/164 |
| 10,874,428 B2 | 12/2020 | Watson |
| 11,864,853 B2 * | 1/2024 | Radgowski ........... A61B 34/30 |
| 2002/0049367 A1 | 4/2002 | Irion et al. |
| 2005/0165272 A1 | 7/2005 | Okada et al. |
| 2005/0209619 A1 | 9/2005 | Johnson et al. |
| 2008/0033450 A1 | 2/2008 | Bayer et al. |
| 2009/0023998 A1 | 1/2009 | Ratnakar |
| 2009/0259097 A1 | 10/2009 | Thompson |
| 2010/0081994 A1 | 4/2010 | Zisow |
| 2010/0198009 A1 | 8/2010 | Farr et al. |
| 2011/0319826 A1 | 12/2011 | Zisow |
| 2012/0289781 A1 | 11/2012 | Pandey |
| 2013/0158348 A1 | 6/2013 | Nobis et al. |
| 2016/0038018 A1 | 2/2016 | Wilson et al. |
| 2017/0319233 A1 | 11/2017 | Fonger et al. |
| 2018/0000499 A1 | 1/2018 | Altman et al. |
| 2019/0059942 A1 | 2/2019 | Watson |
| 2019/0100088 A1 | 4/2019 | Facchinello |
| 2019/0167299 A1 | 6/2019 | Davis et al. |
| 2019/0223905 A1 | 7/2019 | Zeller |
| 2019/0350619 A1 * | 11/2019 | Fujii .................. A61B 1/00009 |
| 2023/0414090 A1 * | 12/2023 | Davis .................... A61B 90/37 |

* cited by examiner

IMAGING CANNULA WITH A HINGED TIP

CROSS-REFERENCE TO RELATED APPLICATIONS

This patent application is a continuation of U.S. application Ser. No. 16/113,225, filed Aug. 27, 2018, entitled "IMAGING CANNULA WITH A HINGED TIP," which claims priority to and the benefit of the filing date of U.S. Provisional Application No. 62/522,014, filed Aug. 30, 2017, entitled "IMAGING CANNULA WITH A HINGED TIP," all of which are incorporated by reference herein in their entireties

TECHNICAL FIELD

The present disclosure is directed to systems utilized in medical procedures and operational methods used during those procedures. More particularly, the present disclosure is directed to a surgical tool and methods of utilizing the surgical tool during a medical procedure.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes a health care provider's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

Minimally invasive surgical procedures performed by teleoperational systems provide many advantages over conventional surgery, however as the size of access points are reduced, so is visualization of the surgical site. Even with advances in surgical access, health care providers still need to see the surgical area in which they work. Conventional minimally invasive surgical procedures are performed using endoscopes introduced through cannulas that carry a camera to capture images that may be displayed to the health care provider. Other cannulas are used to introduce other surgical tools. Accordingly, minimally invasive procedures may require an extra incision through which the endoscope extends.

To reduce the number of incisions in a patient, it would be desirable to provide a cannula having an associated camera thereon that may also be used to introduce other surgical tools.

SUMMARY

In general, the present disclosure is directed to a cannula through which a medical function may be carried out, with the cannula having a hinged tip containing a camera. Certain implementations include the tip and camera in a first position while being advanced through tissue to provide an image to a health care provider, with the tip pivotable about the hinge to move the tip from the cannula opening and to cause the camera to be in a second position during the procedure. Other certain implementations include a first camera and a second camera disposed in the hinged tip. The tip and cameras may be in a first position while the cannula is advanced through tissue, and the tip may pivot about the hinge to a second position away from the cannula opening. The first camera may capture distal images when in the first position and the second camera may capture distal images when the tip is in the second position. Additional certain embodiments of the invention are best summarized by the claims that follow the description.

Some exemplary aspects of the present disclosure are directed to a surgical instrument that includes a cannula having a proximal end, a distal end, and a lumen therethrough. The surgical instrument also includes a camera disposed at the distal end of the cannula to permit visualization of tissue at the distal end of the cannula, and also includes a hinge pivotably coupling the camera to the cannula. The hinge may permit the camera to pivot from a first position where the camera faces a distal direction at the distal end of the cannula to a second position where the camera faces a proximal direction at the distal end of the cannula.

Additional exemplary aspects of the present disclosure are directed to a surgical instrument that includes a cannula having a proximal end, a distal end, and a lumen therethrough. A first camera may be disposed at the distal end of the cannula to permit visualization of tissue at the distal end of the cannula. The surgical instrument also may include a second camera and a displaceable tip carrying the first camera and the second camera. The displaceable tip may be pivotably connected by a hinge to the cannula to pivot between a first position and a second position and carry the first and the second cameras between the first and second positions. The first camera may be disposed to have a field of view in a distal direction when the displaceable tip is in the first position and the second camera disposed to have a field of view in the distal direction when the displaceable tip is in the second position.

Additional exemplary aspects of the present disclosure are directed to a surgical instrument including a cannula having a proximal end, a distal end, and a lumen therethrough, and having a first camera disposed on the cannula and facing in a first direction to permit visualization of tissue in the first direction. The first camera may be arranged to capture images of tissue adjacent the distal end of the cannula. A second camera may be disposed on the cannula and may face in a second direction different than the first direction. In some aspects, a hinge may connect the first and the second cameras to the cannula such that the first camera is disposed to face in a distal direction when the first and the second cameras are in a first position and the second camera is disposed to face in the distal direction when the first and the second cameras are in a second position.

Yet additional exemplary aspects of the present disclosure are directed to methods of visualizing tissue during a medical procedure. Some methods may include capturing images of tissue with a camera carried by a tip attached at a distal end of a cannula while introducing the cannula into a patient, and pivoting the tip and camera from a first position in-line with the cannula to a second position out of line with the cannula to open the cannula. A surgical tool may then be introduced through the cannula.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom . . . e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1A:
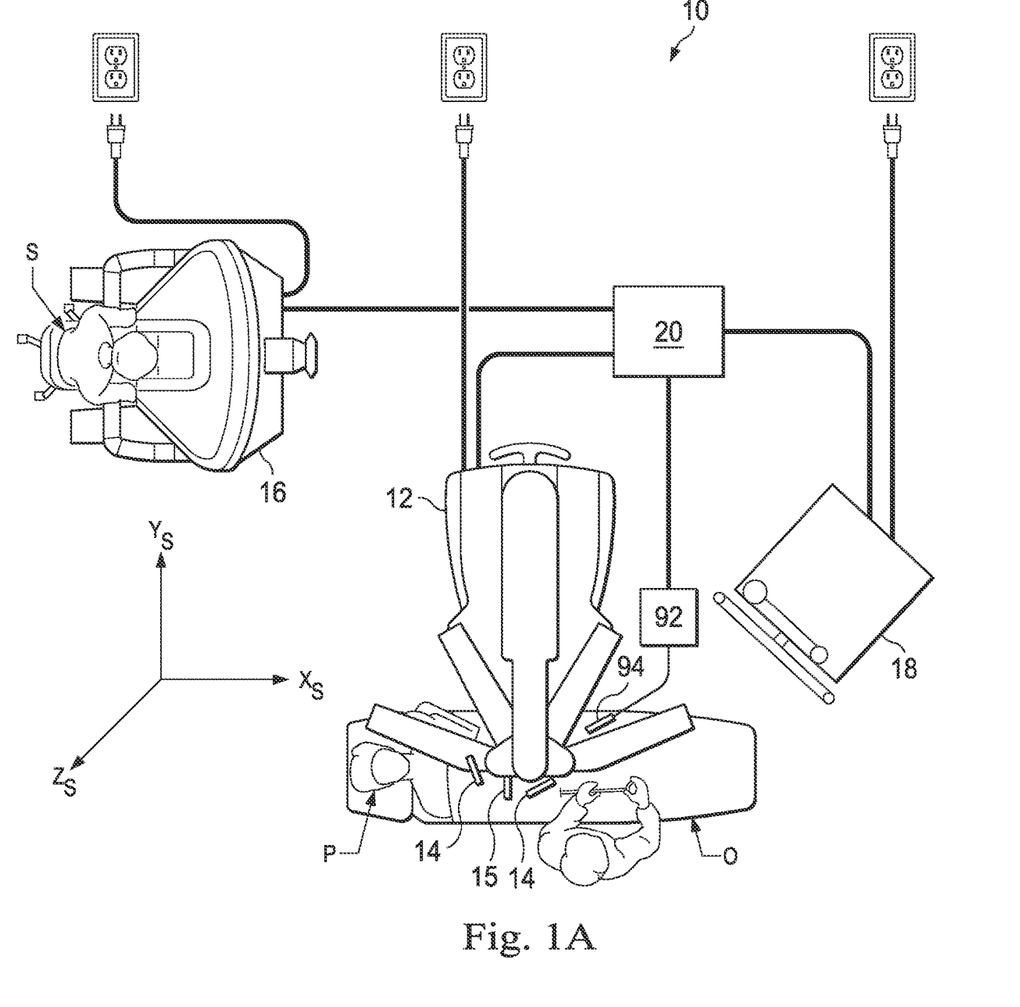
FIG. 1A is a schematic view of a teleoperated medical system in a surgical frame of reference, in accordance with an embodiment of the present disclosure.

Referring to FIG. 1A of the drawings, a teleoperated medical system for use in, for example, medical procedures including diagnostic, therapeutic, or surgical procedures, is generally indicated by the reference numeral 10 and operates within a surgical environment having a surgical frame of reference coordinate system, XS, YS, ZS. As will be described, the teleoperated medical systems of this disclosure are under the teleoperated control of a health care provider. In alternative embodiments, a teleoperated medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperated medical system 10 generally includes a teleoperated assembly 12 mounted to or near an operating table O on which a patient P is positioned. The teleoperated assembly 12 may be referred to as a patient side cart. A medical instrument system 14 and an endoscopic imaging system 15 are operably coupled to the teleoperated assembly 12. An operator input system 16 allows a health care provider or other type of health care provider S to view images of or representing the surgical site and to control the operation of the medical instrument system 14 and/or the endoscopic imaging system 15. A supplemental imaging system 90 including an image processing controller 92 and a minimally invasive imaging cannula 94 may be used with the medical instrument system 14 and endoscopic imaging system 15 as will be described below. Together with the patient side cart, the supplemental imaging system 90 may be known as or may form a part of a patient side system. The endoscopic imaging system 15 provides images of the external surfaces of anatomic structures within the surgical environment. The supplemental imaging system 90 may be an internal imaging system capable of imaging beyond the external surface of the anatomical structures.

The operator input system 16 may be located at a health care provider's console which is usually located in the same room as operating table O. It should be understood, however, that the health care provider S can be located in a different room or a completely different building from the patient P. The health care provider's operator input system 16 includes left and right eye displays for presenting the health care provider S with a coordinated stereo view of the surgical site that enables depth perception. The operator input system 16 further includes one or more input control devices which cause the teleoperated assembly 12 to manipulate one or more instruments or the endoscopic imaging system. The input control devices can provide the same degrees of freedom as their associated instruments 14 to provide the health care provider S with telepresence, or the perception that the input control devices are integral with the instruments 14 so that the health care provider has a strong sense of directly controlling the instruments 14. To this end, position, force, and tactile feedback sensors (not shown) may be employed to transmit position, force, and tactile sensations from the instruments 14 back to the health care provider's hands through the input control devices. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperated assembly to provide the health care provider with telepresence, the perception that the control device(s) are integral with the instruments so that the health care provider has a strong sense of directly controlling instruments as if present at the surgical site. In other embodiments, the control device(s) may have more or fewer degrees of freedom than the associated medical instruments and still provide the health care provider with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperated assembly 12 supports and manipulates the medical instrument system 14 while the health care provider S views the surgical site through the console 16. An image of the surgical site can be obtained by the endoscopic imaging system 15, such as a stereoscopic endoscope, which can be manipulated by the teleoperated assembly 12 to orient the endoscope 15. An electronics cart 18 can be used to process the images of the surgical site for subsequent display to the health care provider S through the health care provider's console 16. The number of medical instrument systems 14 used at one time will generally depend on the diagnostic or surgical procedure and the space constraints within the operating room among other factors. The teleoperated assembly 12 may include a kinematic structure of one or more non-servo controlled links (e.g., one or more links that may be manually positioned and locked in place, generally referred to as a set-up structure) and a teleoperated manipulator. The teleoperated assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperated medical system 10 also includes a control system 20. The control system 20 includes at least one memory and at least one processor (not shown), and typically a plurality of processors, for effecting control between the medical instrument system 14, the endoscopic system 15, the operator input system 16, and monitors on the electronics cart 18. The control system 20 may also receive and process images from the supplemental imaging system 90. The electronics cart 18 may house components of the endoscopic imaging system 15, the supplemental imaging system 90, the control system 20 as well as monitors and processors for processing and displaying captured images.

Some examples of processors may include non-transient, tangible, machine readable media that include executable code that when run by one or more processors may cause the one or more processors to perform the processes of method 600. Some common forms of machine readable media that may include the processes of method 600 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperated assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 20 supports wireless communication protocols such as Bluetooth, IrDA, HomeRF, IEEE 802.11, DECT and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperated assembly 12 to move the medical instrument system(s) 14 and/or endoscopic imaging system 15 which extend into an internal surgical site within the patient's body via openings in the body. Any suitable conventional or specialized servo controller may be used. A servo controller may be separate from, or integrated with, teleoperated assembly 12. In some embodiments, the servo controller and teleoperated assembly are provided as part of a teleoperated arm cart positioned adjacent to the patient's body.

The teleoperated medical system 10 may further include optional operation and support systems (not shown) such as illumination systems, steering control systems, irrigation systems, and/or suction systems. In alternative embodiments, the teleoperated system may include more than one teleoperated assembly and/or more than one operator input system. The exact number of manipulator assemblies will depend on the surgical procedure and the space constraints within the operating room, among other factors. The operator input systems may be collocated, or they may be positioned in separate locations.

Figure 1B:
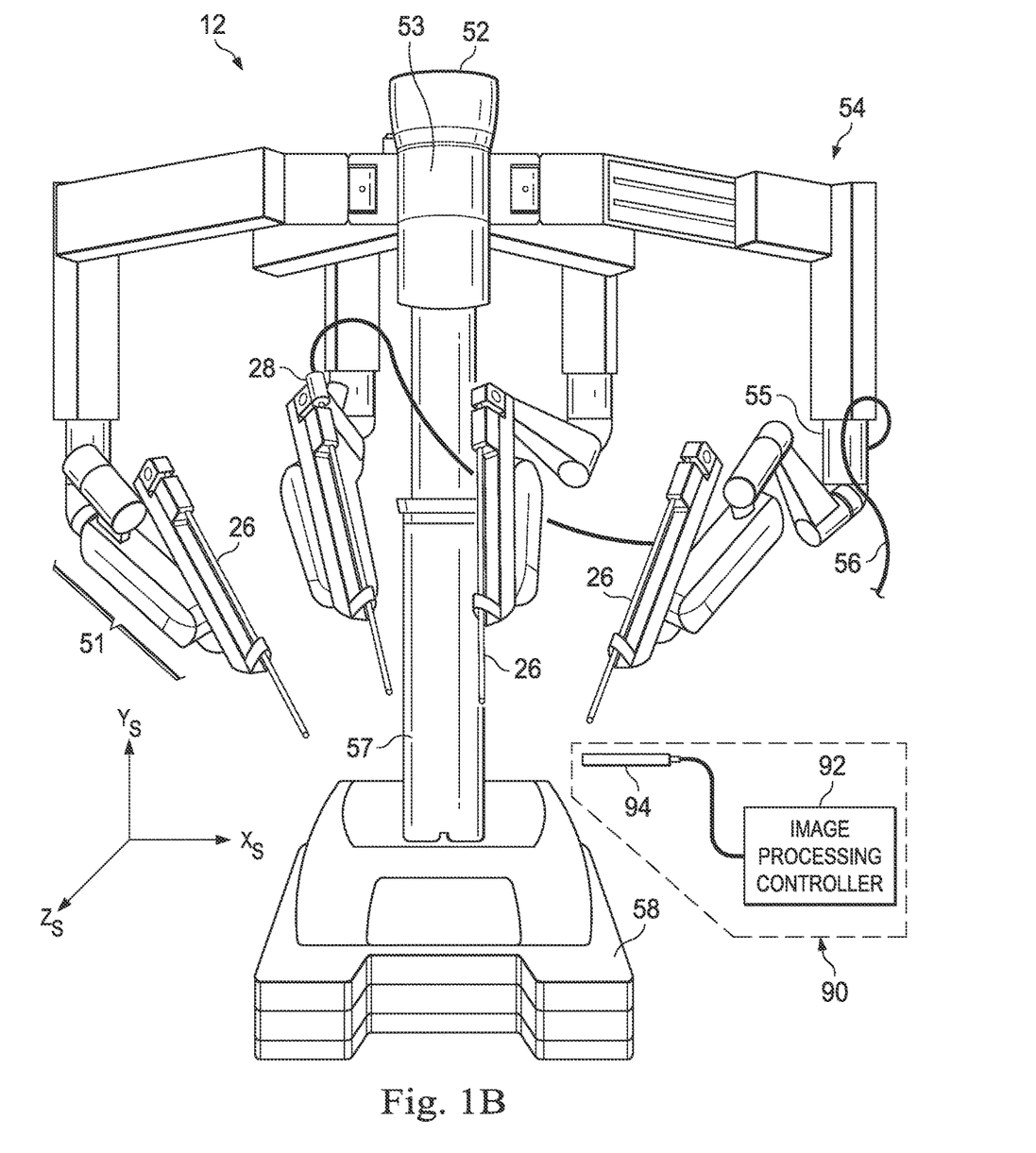
FIG. 1B is a perspective view of patient side systems, according to one example of principles described herein.

FIG. 1B is a perspective view of one embodiment of a teleoperated assembly 12 and a block diagram of a supplemental imaging system 90. The teleoperated assembly 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. As used herein, the term capture or captured images is intended to include still shots, video, and streaming. The imaging device may transmit signals over a cable 56 to the electronics cart 18. Manipulation is provided by teleoperative mechanisms having a number of joints. The imaging device 28 and the surgical tools 26 can be positioned and manipulated through incisions or natural orifices in the patient so that a kinematic remote center is maintained at the incision to minimize the size of the incision. Images of the surgical site can include images of the distal ends of the surgical tools 26 when they are positioned within the field-of-view of the imaging device 28.

The teleoperated assembly 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The teleoperated assembly 12 may also include a telescoping horizontal cantilever 52 for moving the orienting platform 53 in a horizontal direction.

In the present example, each of the arms 54 connects to a manipulator arm 51. The manipulator arms 51 may connect directly to surgical tools 26. The manipulator arms 51 may be teleoperable. In some examples, the arms 54 connecting to the orienting platform are not teleoperable. Rather, such arms 54 are positioned as desired before the health care provider begins operation with the teleoperative components.

The supplemental imaging system 90 may provide imaging functionality that augments and/or complements the functionalities provided by surgical tools 26. The supplemental imaging system 90 includes the image processing controller 92 and the imaging cannula 94 to provide the additional imaging functionality. The imaging cannula 94 may be a minimally invasive instrument sized for insertion into the surgical environment. The supplemental imaging system 90 and the imaging cannula 94 are discussed in greater detail below with reference to FIGS. 2 and 3A-5B.

Endoscopic imaging systems (e.g., systems 15, 90, and/or 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" camera design in which a distal digital sensor such as a one or more charge-coupled device (CCD) or a complementary metal oxide semiconductor (CMOS) device acquire image data. Endoscopic imaging systems may provide two- or three-dimensional images of the endoscopic field of view (i.e. the imaging area) to the viewer. Two-dimensional images may provide limited depth perception. Three-dimensional stereo endoscopic images may provide the viewer with more accurate depth perception. Stereo endoscopic instruments employ stereo cameras to capture stereo images of the field of view of the patient anatomy. An endoscopic instrument may be a fully sterilizable assembly with the endoscope cable, handle and shaft all rigidly coupled and hermetically sealed.

Figure 2:
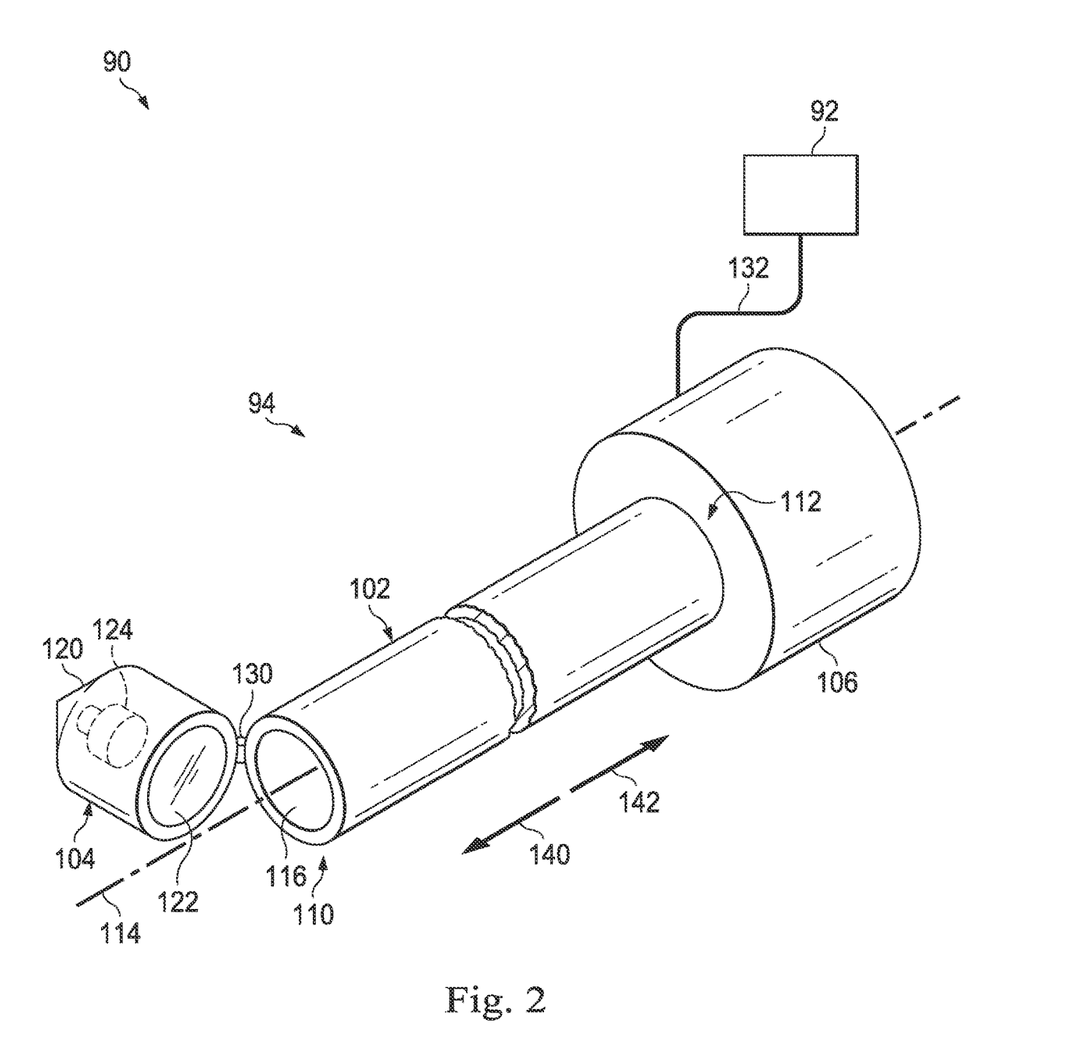
FIG. 2 is a simplified illustration of a cannula with a displaceable tip according to some embodiments.

FIG. 2 is a simplified illustration of the supplemental imaging system 90 including the image processing controller 92 and the image cannula 94. As indicated above, the supplemental imaging system 90 may be incorporated into a teleoperational medical system such as the teleoperated medical system 10 shown in FIGS. 1A and 1B. In other implementations, the supplemental imaging system 90 may be used independently of the teleoperated medical system depicted in FIGS. 1A and 1B. For example, the supplemental imaging system 90 may be used in standalone and/or manually operated applications.

The imaging cannula 94 includes a main body 102, a displaceable tip 104, an optional hub 106, and a displaceable member, described herein as a hinge 130.

The main body 102 is formed as a hollow tube having a distal end 110 and a proximal end 112, and having a lumen 116 passing therethrough from the distal end 110 to the proximal end 112. In the implementation shown, the main body 102 is formed as a cylinder defining and extending along an axis 114. The main body 102 may be insertable into the body of the patient for the delivery or removal of fluid, gathering of data, or providing access to instruments or surgical tools inserted through the lumen 116. Although the diameter of the main body 102 may vary, some implementations include a range of about 14 to 24 gauge. Other sizes are contemplated. In addition, the main body 102 may have any length sufficient to provide access to the desired region of the patient. In some implementations, the length of the main body may be within a range of about 1 inch to 12 inches, although other lengths, both larger and smaller, are contemplated.

The hub 106 may be disposed at the proximal end 112 of the main body 102. The hub 106 may be a flange or collar having a diameter greater than the diameter of the main body 102. In some implementations, the hub 106 may act as a mechanical stop that prevents the imaging cannula 94 from moving distally further into a patient. In some implementations, the hub 106 may be disposed a specific or known distance from the distal end 110 of the main body so that a health care provider is immediately aware of a depth of the distal end 110 of the main body 102 when the hub 106 abuts against the patient's body or other mechanical stop. In some implementations, the hub 106 may be a connector connectable to tubes or other components or systems usable during the surgery.

The tip 104 is disposed at the distal end 110 of the main body 102. The tip 104 may include a pointed leading end 120 and a trailing end 122. The outer diameter of the tip 104 may be sized to substantially match the circular outer diameter of the main body 102. In embodiments where the outer profile of a cross-section of the main body 102 is a shape other than a circle, the outer profile of the tip 104 may be shaped to match that of the outer profile of the main body 102. For example, if the main body 102 had a substantially square cross-section, the outer peripheral edge of the tip 104 may also have a substantially square cross-section. Other cross-sectional shapes are contemplated. The pointed leading end 120 may be sized and arranged to pierce patient tissue when the imaging cannula 94 is introduced into a patient. For example, the tip 104 may be pointed in the manner of a trocar needle in order to puncture the patient's body and pass through tissue to provide access to a region of interest within the patient's body. The trailing end 122 may be sized and arranged to abut against the distal end 110 of the main body 102, and the tip 104 may be sized to cover the lumen 116 of the main body 102.

The tip 104 also may include one or more imaging components, such as a camera 124 to enable the imaging cannula 94 to capture images of tissue, a body cavity, a surgical site which may include surgical tools at a surgical site, or other area of interest within a patient's body. In some implementations, the camera may be used to image tissue through which the imaging cannula 94 passes when introduced to the patient's body. Some implementations include a single camera 124 in the tip 104, while other implementations include two or more cameras as described below. In some implementations, the camera 124 in the tip 104 may be configured to capture still images or a video stream. In some implementations, a live video stream may be transmitted from the camera 124 in the tip 104 to the image processing controller 92 forming a portion of the supplemental imaging system 90. In some implementations, a portion or the entire tip 104 may be formed of a transparent material through which images may be captured. In some implementations, the tip 104, or portions of the tip 104, may be formed of transparent polymers including acrylics poly-carbonates, polyethylenes, polyethylene, composite plastics, including polymer nano-composites, or other materials.

In some implementations, the outer surface of the tip 104 may comprise a lens for the camera 124 disposed in or forming the tip 104. For example, the pointed leading end 120 may have a particular shape that provides focused light by means of refraction to the camera 124 in a manner processable by the image processing controller 92 to generate an image, which may be stored or presented to the health care provider at the operator input system 16. In some instances, the trailing end 122 also has a particular shape to form a lens. For example, the trailing end 122 may include a lens that focuses light into the camera 124 of the tip 104. In other implementations, the trailing end 122 is a flat plane through which the camera 124 may capture images without focus distortion. In such systems, the camera 124 may include lenses independent of the trailing end 122 of the tip 104. Naturally, any convex shape of the trailing end 122 may be less pronounced than the curved shape of the leading end 120.

The tip 104 may be connected to the main body 102 by a displacing element shown and described herein as a hinge 130. In this embodiment, the hinge is disposed at the distal end 110 of the main body 102 connecting the main body 102 to the tip 104. In some implementations, the hinge 130 permits the tip 104 to pivot from a first position where the pointed leading end 120 of the tip 104 faces in the distal direction indicated by the arrow 140 to a second position where the pointed leading end 120 of the tip 104 faces a proximal direction indicated by the arrow 142. These positions may be generally referred to as a closed position where the tip is in line with the lumen 116 and the pointed leading end extends in the distal direction 140 and as an open position where the tip 104 is out of alignment with the lumen 116. The purpose of this displaceable tip 104 will become apparent in accordance with the further description below.

The hinge 130 may be any type of hinge suitable for pivoting the tip 104 from the closed position to the open position. In some implementations, the hinge 130 includes a pivot hinge acting as a mechanical bearing connecting the tip 104 to the main body 102. In some implementations, the hinge provides a fixed axis of rotation about which the tip 104 pivots to move from the closed position covering the lumen 116 of the main body 102 to the open position where the lumen 116 is open or accessible.

Depending on the implementation, the hinge 130 may be a standard hinge having two leaves, each with at least one knuckle, and with a pin extending through the knuckles and defining a pivot axis about which the leaves rotate. Particularly, the knuckles may extend from the leaves and wrap around the pin. Other types of hinges may be used. For example, some implementations of the imaging cannula 94 include concealed hinges embedded in the distal edge of the main body 102 and the trailing end 122 of the tip 104. Such a concealed hinge ensures that the tip 104 may properly abut against the distal end 110 of the main body 102 in a manner that maintains the hinge 130 at a position within the outer boundary of the main body 102. So doing may ensure that the hinge 130 is not exposed to rub against, tear, or introduce additional trauma to tissue as the cannula 94 is introduced through tissue into the patient.

In some cases, the hinge 130 may be a biased hinge that may bias the tip 104 toward the closed position where the pointed leading end 120 of the tip 104 faces in the distal direction indicated by the arrow 140. In other cases, the hinge 130 may be a biased hinge that may bias the tip 104 toward the open position where the pointed leading end 120 of the tip 104 faces the proximal direction indicated by the arrow 142. In yet other cases, the hinge 130 may be arranged to be biased toward both the closed position and the open position. In such cases, the hinge 130 may require a relatively higher applied force to move the tip 104 away from the closed position toward the open position, but as the tip 104 approaches the open position, the biasing force takes over and snaps the tip 104 to the open position. Likewise, the same biasing force toward the open position would need to be overcome in order to move the tip to the closed position. As the tip 104 approaches the closed position, the biasing force toward the closed position may snap the tip 104 toward the closed position.

In some instances, the hinge 130 may be a spring hinge biasing the tip as described. That is, depending on the implementation, the spring hinge may include a spring biasing the tip 104 to a position away from the distal end 110 of the main body 102, to a position toward the distal end 110 of the main body, or both. Accordingly, the tip 104 may be biased to an open position, a closed position, or biased toward at least two discrete positions.

In some embodiments, the hinge is a flexure hinge formed as a compliant mechanism. The flexure hinge may be formed of the same material as the tip 104 or may be attached to the tip 104 and the main body 102 using an adhesive, screws, ultrasonic welding, or other attachment mechanism. In some implementations, the flexure hinge may bias the tip 104 toward one, two, or more positions. For example, in some implementations, the flexure hinge biases the tip 104 toward the closed position and also biases the tip 104 toward the open position.

In implementations where the hinge 130 biases the tip 104 to discreet positions that correspond with the closed position and the open position, the discrete positions may be established to be those that direct the camera 124 carried in the tip 104 to provide a desired field of view. In some implementations, the discrete positions are first and open positions arranged to be 180 degrees from each other as will be described with reference to FIGS. 3A and 3B. Other implementations have discrete positions at 90 degrees from each other, at 120 degrees from each other, or at other angles.

In the implementation shown, the cannula 94 is connected to the image processing controller 92 via a cable 132. The cable 132 may extend to the camera 124, and may be arranged to carry data signals from the camera 124 to the image processing controller 92. As indicated above, the image processing controller 92 may be in communication with or may form a part of the control system 20 of the teleoperated medical system 10. In some implementations, the image processing controller 92 may be disposed in the tip 104 with the camera 124. In one implementation, the camera 124 includes a light detector or image sensor, while the image processing occurs at the image processing controller 92. In other implementations, the camera 124 includes the light detector or image sensor and the processor and memory functions to enable the camera to capture images. The cable 132 may also carry commands to the camera 124. For example, if the camera 124 is capable of an optical zoom, then control signals from the health care provider to the camera may be carried by the cable 132. In some implementations, the cable 132 may extend down the lumen 116 of the main body 102, may be embedded in the wall of the main body 102, or may be otherwise situated to physically connect the camera 124 to the image processing controller 92. In some implementations, the camera 124 includes or is in communication with a wireless transmitter or transceiver that may transmit or stream signals of captured images to the image processing controller 92 for storage or display to the health care provider.

Figure 3A:
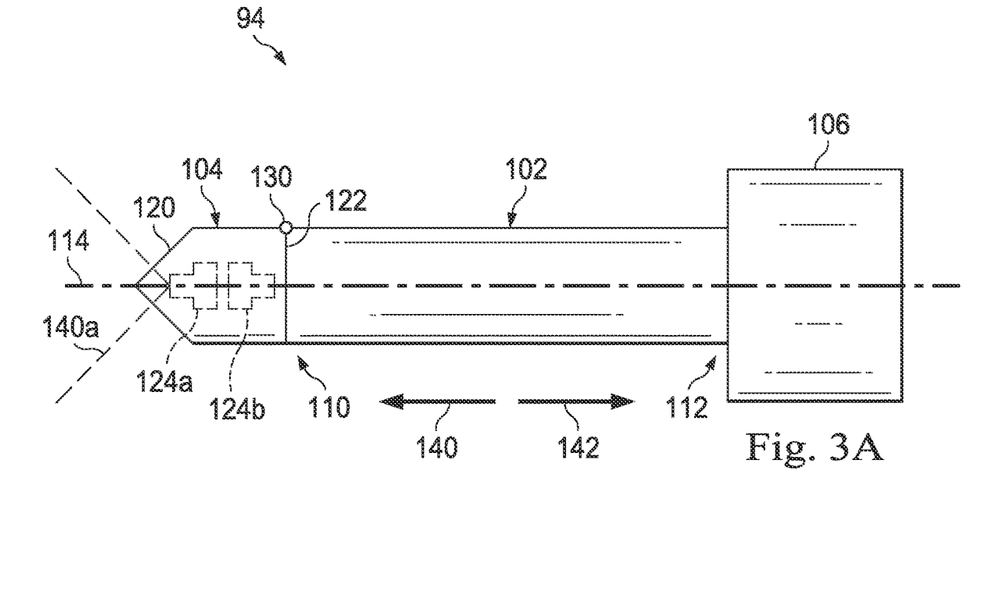
FIG. 3A is a simplified illustration of a cannula with a tip in a first position for the insertion through tissue of a patient according to some embodiments.
Figure 3B:
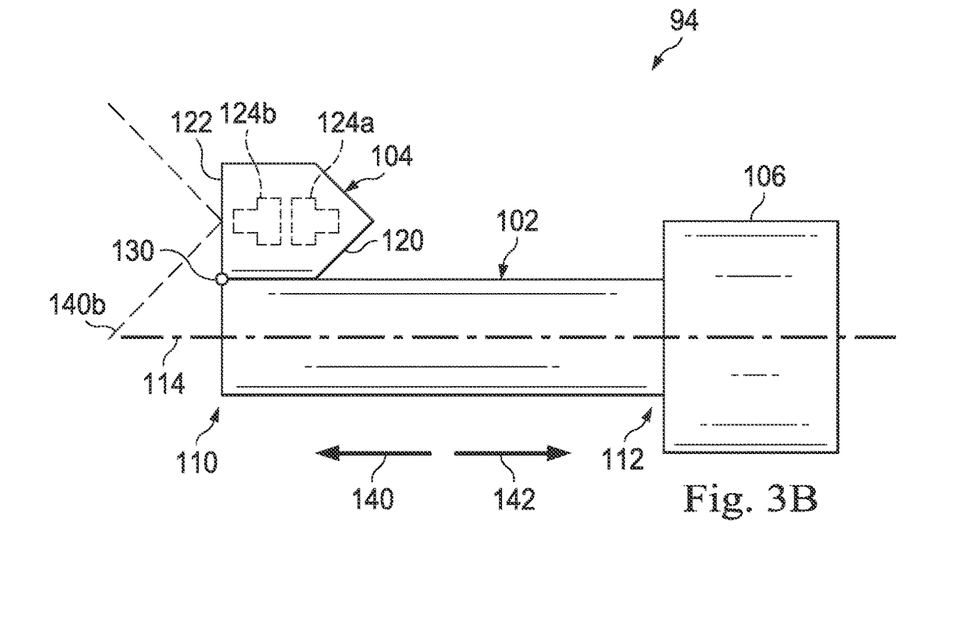
FIG. 3B is a simplified illustration of a cannula with a tip in a second position accommodating the passage of surgical tools therethrough according to some embodiments.

FIGS. 3A and 3B show a side view of the imaging cannula 94. In FIG. 3A, the tip 104 is disposed in a closed position, with the tip 104 in-line with the main body 102 and covering its lumen 116 (shown in FIG. 2). In FIG. 3B, the tip 104 is disposed in a open position, with the tip 104 disposed out of line with the lumen 116. In this implementation, the tip 104 is disposed adjacent the side or exterior surface of the main body 102. In the open position, a health care provider or the teleoperated assembly 12 may introduce surgical tools 26 (FIG. 1B) through the lumen 116 of the imaging cannula 94 to perform a medical task or procedure. Accordingly, in the implementation shown, the tip 104 pivots 180° about the hinge 130 from the closed position shown in FIG. 3A to the open position shown in FIG. 3B.

The position of the camera 124 in the tip 104 is also apparent in these Figures. In FIG. 3A, the tip 104 includes two cameras 124, disposed back to back. For explanatory purposes, FIG. 3A refers to a first camera 124a and a second camera 124b. Since the tip 104 is formed of a clear or transparent material, the cameras 124a, 124b are able to image through the material of the tip 104 and capture images.

FIG. 3A shows the cannula 94 ready for insertion through skin and tissue of the patient to a cavity undergoing examination or treatment. Accordingly, with the tip 104 disposed in-line with the axis 114 (or in a closed position), the field-of-view 140a from the camera 124a appears in the distal direction 140 in front of the tip 104. Accordingly, as the cannula 94 is inserted into the patient, the camera 124a can image the tissues that come in contact with the tip 104. This may enable a healthcare provider to determine what tissues are being transected by the imaging cannula 94. In addition, this may enable the user to determine when the distal tip 104 has reached the interior of the patient's body. For example, it may become visually apparent to a health care provider when the distal tip 104 enters a cavity to undergo treatment.

FIG. 3B shows the cannula 94 in position to perform a surgical task to provide access to the interior of the patient. Here, the tip 104 is rotated 180° about the hinge 130. Accordingly, the camera 124a, and the leading end 120 of the tip 104 are pivoted about the hinge 130 to face the proximal direction 142. Here, the camera 124b has also pivoted from a position facing the proximal direction 142 to a position facing the distal direction 140. Accordingly, the camera 124b provides a field-of-view 140b facing the distal direction 140. Because of this arrangement, the camera 124b may provide visualization to a health care provider of a surgical site, including visualization of surgical tools that may be inserted through the imaging cannula 94. In some implementations, the tip 104 may be biased toward the discrete positions shown in the manner described herein. In this implementation, one discrete position may be the pivoted position in FIG. 3B with the tip 104 rotated 180°. In implementations with a hinge having two discrete positions, a first discrete position may be the position shown in FIG. 3A and a second discrete position may be the position shown in FIG. 3B. In some implementations, the tip 104 may be rotated by a surgical tool introduced through the lumen 116 (FIG. 2) to abut against and displace the tip 104 about the hinge 130.

Alternative implementations may include discrete positions that are not 180° apart. As one example, a first discrete position of the tip 104 may be the position shown in FIG. 3A, and a second discrete position of the tip 104 may be a position rotated 90° from the position shown in FIG. 3A. In this instance, where two cameras are used, the camera 124b also may be pivoted by 90 degrees so as to provide a field-of-view facing in the distal direction 140.

In one example using a spring hinge, the tip 104 may be biased to the position shown in FIG. 3B and not biased to the position shown in FIG. 3A. In such an implementation, a healthcare provider may prepare for surgery by manually aligning the tip 104 in the position shown in FIG. 3A and placing the tip 104 against the patient's tissue so that the tissue resistance is greater than the spring force of the hinge 130. In such a condition, the tissue itself may maintain the tip 104 in the closed position shown in FIG. 3A during the time period that the cannula 94 is being advanced through the patient tissue. Accordingly, the health care provider could view the tissue being transected by the cannula. When the tip 104 enters a cavity in the patient, the resistance to the spring force of the hinge 130 may be decreased, and the spring hinge may rotate or pivot the tip 104 to the position shown in FIG. 3B. As such, the cannula 94 may be self-opening.

FIGS. 3A and 3B show the cannula 94 using two cameras 124a, 124b to capture images with field of views in the distal direction 140. In some implementations, both cameras 124a and 124b continuously stream images to the image processing controller 92, which may form a part of the control system 20. The control system 20 may then stream images to the operator input system 16 for live viewing by the health care provider S (FIG. 1.). In some implementations, the operator input system 16 may be arranged to receive inputs from a healthcare provider to command the control system 20 to switch viewpoints to change the display between images captured by the first camera 124a and images captured by the second camera 124b. In other implementations, the operator input system may be arranged to activate or stream from one camera at a time.

Figure 4A:
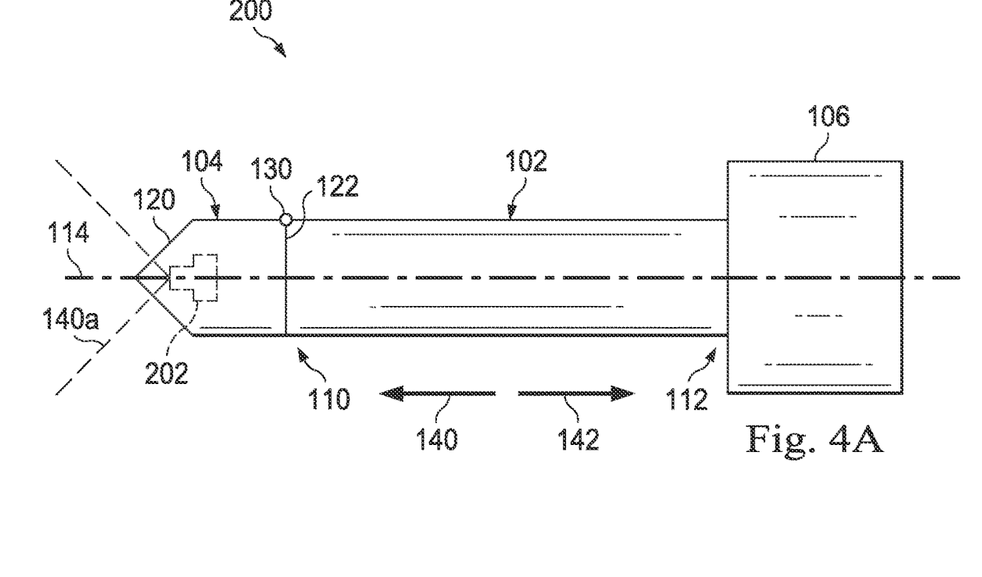
FIG. 4A is a simplified illustration of a cannula with a tip in a first position for the insertion through tissue of a patient according to some embodiments.
Figure 4B:
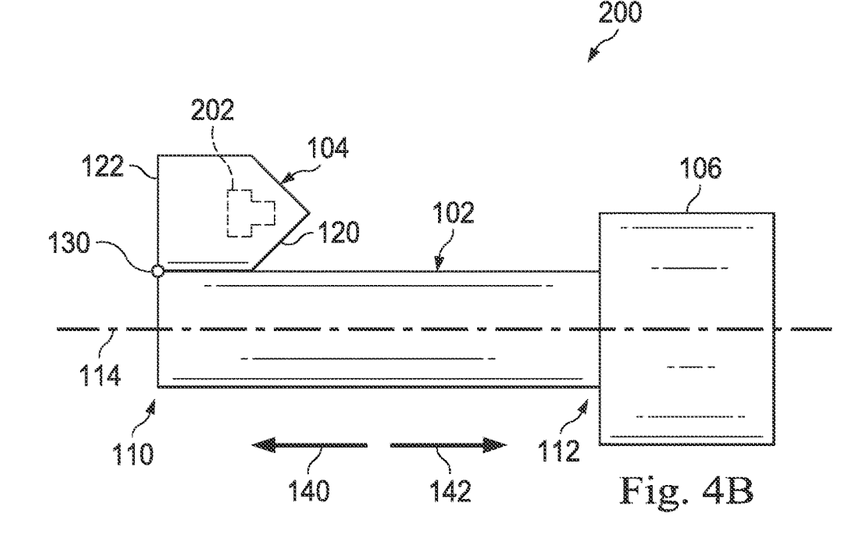
FIG. 4B is a simplified illustration of a cannula with a tip in a second position accommodating the passage of surgical tools therethrough according to some embodiments.

FIGS. 4A and 4B show another imaging cannula 200 with a single camera 202 facing one direction. The imaging cannula 200 differs from the cannula 94 only in that the tip 104 includes a single camera 202. Accordingly, for simplicity, other portions of the imaging cannula 200 will not be re-described. The camera 202 has a field-of-view 140a facing in the distal direction 140 in FIG. 4A. However, with the tip 104 pivoted about the hinge 130 in FIG. 4B, the field-of-view is now facing in the proximal direction 142. Accordingly, the cannula 200 may be unable to image the surgical site during the surgical procedure.

Figure 5A:
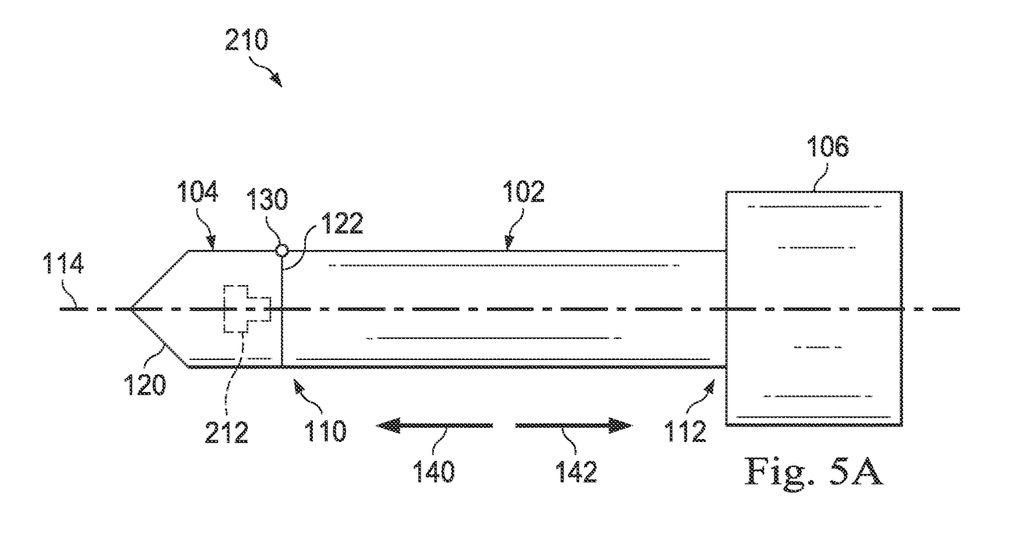
FIG. 5A is a simplified illustration of a cannula with a tip in a first position for the insertion through tissue of a patient according to some embodiments.
Figure 5B:
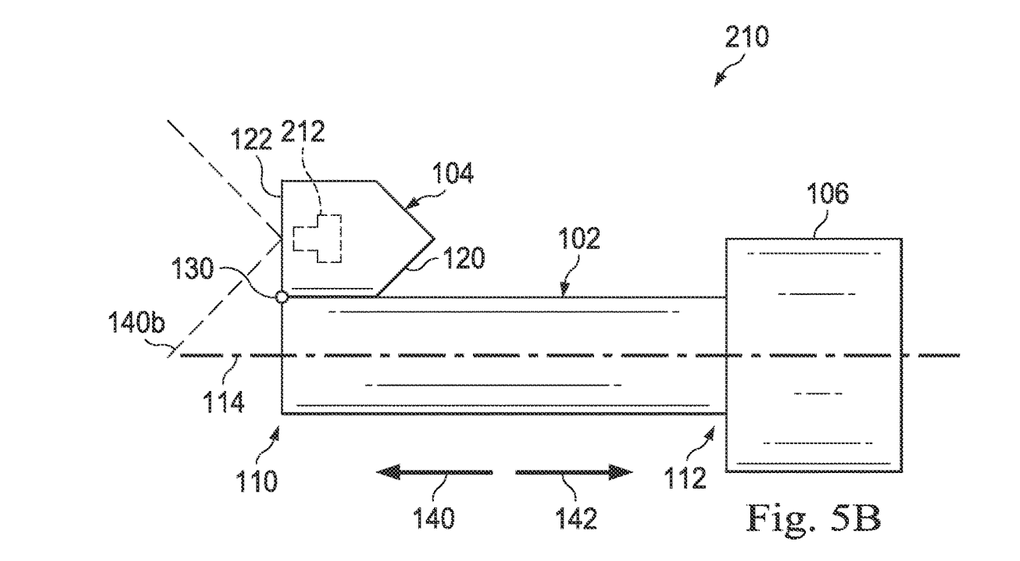
FIG. 5B is a simplified illustration of a cannula with a tip in a second position accommodating the passage of surgical tools therethrough according to some embodiments.

FIGS. 5A and 5B show another imaging cannula 210 with a single camera 212 facing the direction opposite that shown in FIGS. 4A and 4B. The imaging cannula 210 differs from the cannula 200 only in that the tip 104 includes the single camera 212 facing the direction opposite that shown in FIGS. 4A and 4B. Again, for simplicity, other portions of the imaging cannula will not be re-described. The camera 212 has a field-of-view 140b facing in the distal direction 140 only when the tip 104 is pivoted to an open position where the cannula 210 is open.

Figure 6:
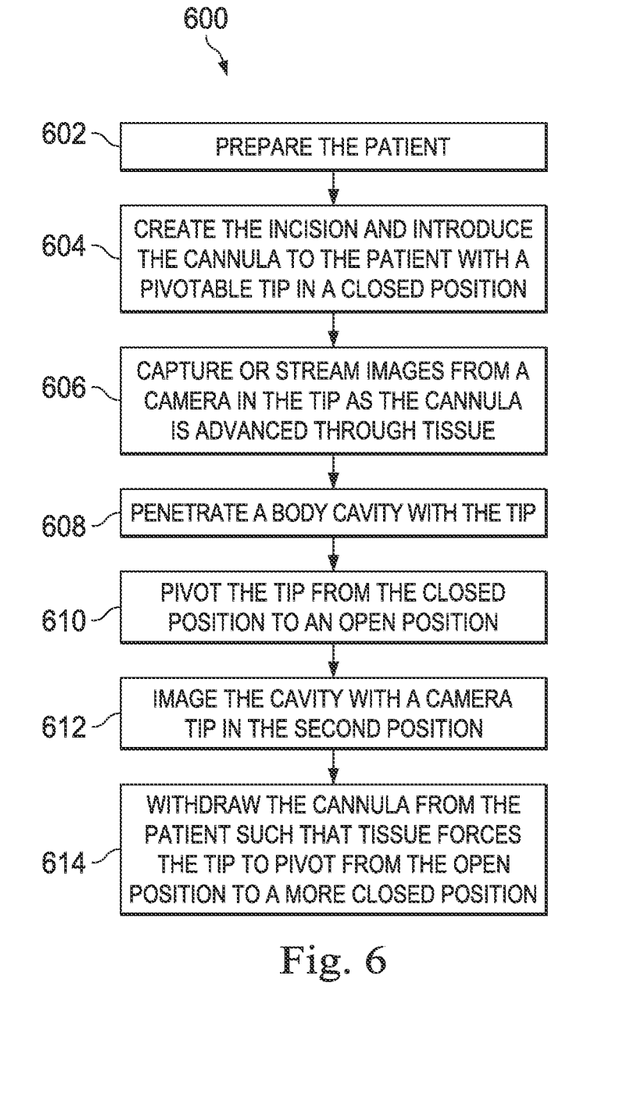
FIG. 6 is a simplified flow diagram of a method of imaging tissue during a medical procedure according to some embodiments.

FIG. 6 is a simplified diagram of a method 600 for imaging tissue of a patient during a surgical procedure. According to some embodiments, the method 600 may be performed using, for example, the teleoperated medical system 10 as described herein. The method may begin at 602 by preparing the patient for the surgical procedure. At 604, the method includes creating an incision and introducing the cannula with a pivotable tip in a closed position. As used herein, the closed position is a position where the tip covers the lumen of the cannula. Creating the incision may include cutting tissue to create an opening through which the cannula may pass, or may include piercing the skin and tissue with the pointed tip of the cannula. Introducing the cannula to the patient with the tip in the closed position may include simply advancing the tip into patient tissue when the tip is biased to the closed position. Alternatively, it may include orienting the tip against a biasing force, such a biasing force of the hinge, to be in the closed position, and then placing the tip against the patient in order to maintain the tip in the closed position while the tip is introduced to the patient. Accordingly in such instances, the force of patient tissue on the tip may be greater than the biasing force to maintain the tip of the closed position.

At 606, the imaging cannula may capture or stream images from a camera in the tip as it advances through the patient tissue. The tip may include one, two, or more cameras arranged to capture images of portions of the surgical procedure. In some implementations, two cameras are arranged back to back in the cannula tip. These cameras may have different lens arrangements that may include or cooperate with the shape of the tip surfaces to provide images useful to the health care provider. Some implementations include a camera arranged to capture clear images of tissue in contact with the tip taking into account the angled surfaces forming the pointed leading end of the tip. Some implementations include a first camera arranged to clearly capture images of tissue in contact with the tip and a second camera arranged to clearly capture images of tissue or instruments spaced from the tip. At 606, the imaging cannula may image tissues that come in contact with the tip. In so doing, the user may be able to determine what tissues are being transected by the cannula as well as determine when the cannula reaches a desired location at the interior of the patient's body.

At 608, the tip may penetrate a body cavity or otherwise arrive at a desired location. In some implementations, entry into the body cavity may be visible and apparent based on images from the camera in the tip of the cannula.

At 610, the camera tip may pivot from the closed position to an open position. As described herein, the open position may be a position where the tip is not aligned with the lumen of the cannula. In some implementations, the open position may be a position where the tip is pivoted 180° and is adjacent to and/or in contact with an exterior surface of a main body of the cannula. In some implementations, the tip may pivot in response to a surgical tool introduced from a proximal end of the cannula through the cannula to make contact against a proximally facing portion of the tip when the tip is in the closed position. Additional application of force may pivot the tip from its closed position in-line with the lumen of the cannula to an open position not in-line with the lumen of the cannula. As described herein, some hinges bias the tip to discrete positions. Accordingly, applying a force with a surgical tool against the tip may displace the tip from the lumen of the cannula, and the biasing hinge may continue to apply a biasing force to pivot the tip to a pre-established discrete position. In some implementations, this discrete position may be a position 180° about a pivot axis from the closed position to an open position.

In embodiments having a camera that faces the proximal direction when the tip is in the closed position, 180° pivoting may move the camera to face the distal direction. In this position, the camera may capture images distal of the distal end of imaging cannula.

At 612, the imaging cannula may capture or stream images with a camera while the tip is in the open position. This may provide a distally facing field-of-view allowing imaging of an interior of a body cavity. This may also allow a user to guide and observe the entry of other cannulae or instruments.

Upon completion of a surgical procedure, at 614, the cannula may be withdrawn from the patient. Because of the pivotable nature of the tip, tissue may cause the tip to pivot from the open position to a position at least partially aligned with the lumen of the cannula. The cannula and tip may then be withdrawn from the patient.

Any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A surgical instrument, comprising:
a cannula having a proximal end, a distal end, and an access lumen therethrough;
a camera disposed at the distal end of the cannula to permit visualization of tissue;
a distal tip comprising a pointed leading end alignable with a distal end of the cannula and shaped to pierce and separate tissue, the distal tip comprising an optically clear material through which the camera captures images of the tissue; and a hinge pivotably coupling the camera to the cannula, the hinge permitting the camera to pivot from a first position to capture images, with the camera, in a first direction aligned with a longitudinal axis of the cannula through the distal tip while the distal tip blocks access to a patient through the lumen to a second position to capture images, with the camera, in a second direction not aligned with the longitudinal axis of the cannula while the distal tip does not block access to the patient through the lumen and where the distal tip permits access to the patient through the lumen, wherein the first direction is a distal direction, and wherein when the camera is in the first position, a field-of-view of the camera is in the first direction, and when the camera is in the second position, the field-of-view of the camera is in the second direction.

2. The surgical instrument of claim 1, wherein the hinge is structurally configured to permit the camera to pivot about 90 degrees.

3. The surgical instrument of claim 1, wherein the hinge is structurally configured to permit the camera to provide the field-of-view distal of the cannula.

4. The surgical instrument of claim 1, wherein the hinge comprises a pin defining a pivot axis for the camera.

5. The surgical instrument of claim 1, wherein the hinge is a concealed hinge within a boundary of the cannula.

6. The surgical instrument of claim 1, wherein the hinge is configured to maintain the camera in a discrete position.

7. The surgical instrument of claim 1, wherein the second direction is a proximal direction, and wherein the camera is configured to capture images in the distal direction when in the first position and to capture images in the proximal direction when in the second position.

8. The surgical instrument of claim 1, wherein the hinge is biased to position the camera in the first position.

9. The surgical instrument of claim 1, wherein the hinge is biased to position the camera in the second position.

10. The surgical instrument of claim 1, wherein the hinge is biased to position the camera in the first position and to position the camera in the second position.

11. The surgical instrument of claim 1, wherein the hinge is biased to position the camera in a plurality of discrete positions, wherein the plurality of discrete positions comprises the first position and the second position.

12. A surgical instrument, comprising:
a cannula having a proximal end, a distal end, and an access lumen therethrough;
an image capture component disposed at the distal end of the cannula to permit visualization of tissue, the image capture component comprising at least one camera;
a distal tip comprising a pointed leading end alignable with a distal end of the cannula and shaped to pierce and separate tissue, the distal tip comprising an optically clear material through which the image capture component captures images of the tissue; and
a hinge pivotably coupling the image capture component to the cannula, the hinge permitting the image capture component to pivot from a first position where the at least one camera of the image capture component has a field-of-view in a direction substantially perpendicular to a longitudinal axis through a distal region of the cannula to a second position where the at least one camera of the image capture component has a field-of-view in a distal direction.

13. The surgical instrument of claim 12, wherein the image capture component comprises a first camera facing a first direction and a second camera facing a second direction offset by about 90 degrees from the first direction.

14. The surgical instrument of claim 12, wherein the image capture component is disposed in-line with the cannula and captures images through the distal tip when the image capture component is in the first position and wherein the image capture component is disposed not in-line with the cannula when the image capture component is in the second position.

15. The surgical instrument of claim 12, wherein the hinge is a concealed hinge within a boundary of the cannula.

16. The surgical instrument of claim 15, wherein the hinge comprises a pin that defines a pivot axis of the hinge.

* * * * *

UNITED STATES PATENT AND TRADEMARK OFFICE
CERTIFICATE OF CORRECTION

| | | |
|---|---|---|
| PATENT NO. | : 12,076,044 B2 | Page 1 of 1 |
| APPLICATION NO. | : 17/114292 | |
| DATED | : September 3, 2024 | |
| INVENTOR(S) | : Jason Paul Watson | |

It is certified that error appears in the above-identified patent and that said Letters Patent is hereby corrected as shown below:

In the Specification

Column 13, Line 39, change "dosed" to -- closed --

Signed and Sealed this
First Day of July, 2025

Coke Morgan Stewart
*Acting Director of the United States Patent and Trademark Office*